United States Patent
Maruoka et al.

(10) Patent No.: US 6,672,141 B2
(45) Date of Patent: Jan. 6, 2004

(54) VISCOELASTIC CHARACTERISTIC VALUE-MEASURING APPARATUS AND METHOD OF MEASURING VISCOELASTIC CHARACTERISTIC VALUE

(75) Inventors: Kiyoto Maruoka, Hyogo (JP); Jun Nishibayashi, Hyogo (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 0 days.

(21) Appl. No.: 09/951,215

(22) Filed: Sep. 11, 2001

(65) Prior Publication Data

US 2002/0043099 A1 Apr. 18, 2002

(30) Foreign Application Priority Data

Sep. 11, 2000 (JP) .......................... 2000-275405

(51) Int. Cl.[7] .............................................. G01N 11/10
(52) U.S. Cl. ...................................... 73/54.39; 73/12.01
(58) Field of Search ........................... 73/12.01, 760, 73/841, 54.39

(56) References Cited

U.S. PATENT DOCUMENTS

| | | | |
|---|---|---|---|
| 6,023,976 A | * | 2/2000 | Borza et al. .................. 73/598 |
| 6,109,093 A | * | 8/2000 | Albertini et al. ............ 73/12.08 |
| 6,116,077 A | * | 9/2000 | Albertini et al. ............ 73/12.05 |
| 6,422,952 B1 | * | 7/2002 | Maruoka et al. ............ 473/351 |

FOREIGN PATENT DOCUMENTS

| | | |
|---|---|---|
| EP | 1 065 492 A2 | 1/2001 |
| GB | 2 364 132 A | 1/2001 |

OTHER PUBLICATIONS

"Impact Engineering", Published by Nikkon Kogyo Newspaper Ltd. pp. 173–183, (1988).

(Nakagawa et al, Lecture thesis of 16th series of Chugoku Branch of Japan Design Engineering Society Association, pp. 25–29, Jun. 20, 1998.

* cited by examiner

*Primary Examiner*—Max Noori
(74) *Attorney, Agent, or Firm*—Birch, Stewart, Kolasch & Birch, LLP

(57) ABSTRACT

In a viscoelastic characteristic value-measuring apparatus, using a split Hopkinson's bar, a first strain gauge (7) and a second strain gauge (9) are installed on an input bar (3) which is hit with a impact bar. A third strain gauge (11) and a fourth strain gauge (13) are installed on an output bar (5) which is connected with the input bar (3) through a specimen (20) put between the input bar (3) and the output bar (5). The length of the input bar is set to not less than 1000 mm nor more than 2500 mm. The length of said output bar is set to not less than 700 mm nor more than 2200 mm. The propagation speed of a strain in the input bar and the output bar is set to not less than 1200 m/s nor more than 1800 m/s.

9 Claims, 4 Drawing Sheets

VISCOELASTIC CHARACTERISTIC VALUE-MEASURING APPARATUS AND METHOD OF MEASURING VISCOELASTIC CHARACTERISTIC VALUE

BACKGROUND OF THE INVENTION

1. Field of the Invention

The present invention relates to an apparatus and a method of measuring viscoelastic characteristic values such as Young's modulus, a loss factor, and the like of a viscoelastic material such as synthetic resin, crosslinked rubber, and the like. More particularly, the present invention is intended to measure viscoelastic characteristic values of a soft viscoelastic material accurately by using a so-called split Hopkinson's bar.

2. Description of the Related Art

In recent years, to analyze the deformation and behavior of an object to which an impact is applied, simulation is used rather than measurement. In the simulation, it is necessary to perform substitutions of the viscoelastic characteristic values (parameter) such as the Young's modulus, the loss factor, and the like of the object. The parameter is classified into a static parameter and a dynamic parameter. Because the deformation and behavior of the object is dynamic, the dynamic parameter measured in a state close to the deformation and behavior is effective for the simulation. The measurement of the dynamic parameter is also important for apprehending the characteristic of the object.

As means for measuring the dynamic parameter, an apparatus using the split Hopkinson's bar is known. The split Hopkinson's bar is used in the field of a metal material (see page 173–183 of "Impact Engineering" published by Nikkan Kogyo Newspaper Ltd. on Oct. 28, 1989) or the like. In the apparatus using the split Hopkinson's bar, a impact bar, an input bar, and an output bar all made of metal are arranged in a straight line, with a specimen held between the rear end of the input bar and the front end of the output bar, and a strain gauge is installed on each of the input bar and the output bar (the input bar and the output bar may be hereinafter referred to as stress bar). In measuring the viscoelastic characteristic of the specimen, the impact bar is brought into collision with the front end of the input bar. A strain wave generated at this time propagates from the input bar to the specimen and the output bar. The following three waves are measured with the strain gauges installed on the input bar and the output bar to compute the viscoelastic characteristic value of the specimen: An incident strain wave progressing in the input bar to its rear end, a reflected strain wave reflected from the rear end of the input bar to the front end thereof and a reflected strain wave reflected from the rear end of the specimen to the front end thereof after the incident strain wave passes through the specimen, and a transmitted strain wave which advances from the input bar to the rear end of the output bar through the specimen.

It is to be noted that in description made below the incident strain wave, the reflected strain wave, and the transmitted strain wave are abbreviated as a "strain wave" as necessary.

The measuring apparatus is capable of measuring the characteristic value of a metal material but has difficulty in measuring the viscoelastic characteristic value of a polymer such as synthetic resin, crosslinked rubber, and the like. When the specimen is made of the polymer, there is a large difference between the characteristic impedance of the specimen and that of the stress bar made of metal. Consequently the reflected strain wave is generated. Thus in measuring the viscoelastic characteristic value of the polymer, it is necessary to select the stress bar made of a material whose characteristic impedance is not different much from that of the specimen.

A viscoelastic characteristic value-measuring apparatus using the stress bar made of polymethyl methacrylate is disclosed by Nakagawa of Hiroshima University and others on pages 25–29 of lecture thesis of 16th series of Chugoku Branch of Japan Design Engineering Society Association. It is possible to reduce the difference between the impedance of the specimen made of the polymer and that of the stress bar by composing the stress bar of the polymer such as polymethyl methacrylate. Thereby it is possible to measure the viscoelastic characteristic value of the specimen made of the polymer.

Unlike the stress bar made of metal, the strain wave generated in the stress bar made of the polymer attenuates greatly. For example, the incident strain wave progressing to the specimen from the input bar is measured with a strain gauge installed on the input bar and attenuates a little before it reaches the rear end of the input bar. Thus, it is impossible to correctly measure the incident strain wave at the rear end of the input bar. Similarly, it is impossible to correctly measure the reflected strain wave reflected from the rear end of the input bar to the front end of the input bar and the reflected strain wave reflected from the rear end of the specimen to the front end of the input bar after the incident strain wave passes through the specimen, and the transmitted strain wave which passes through the output bar from the rear end of the specimen.

In the viscoelastic characteristic value-measuring apparatus disclosed by Nakagawa and others, two strain gauges are installed on each of the input bar and the output bar to solve the problem of the damp of the stress bar made of the polymer. That is, a transmission function is derived from the incident strain wave, the reflected strain wave, and the transmitted strain wave measured with the two strain gauges. From the transmission function, the strain amount of each of the incident strain wave at the rear end of the input bar, the reflected strain wave at the rear end of the input bar, and the transmitted strain wave at the front end of the output bar are estimated. The viscoelastic characteristic value-measuring apparatus is capable of measuring the viscoelastic characteristic value of the specimen when the specimen deforms greatly at high speed (maximum strain speed: 100–8000 per second) and in a large amount (maximum deformation amount is in the range from 0.1%–30%).

The viscoelastic characteristic value-measuring apparatus is capable of correctly measuring the viscoelastic characteristic value of a comparatively hard polymer, but has a large error in measuring the viscoelastic characteristic value of a particularly soft viscoelastic material. That is, the viscoelastic characteristic value-measuring apparatus is incapable of obtaining a correct viscoelastic characteristic value. The error is attributed to the fact that as the specimen becomes softer, the difference between the propagation speed of a strain in the specimen and that of a strain in the input bar and the output bar disposed forward and rearward from the specimen respectively becomes increasingly large.

That is, in the case of the specimen made of the particularly soft viscoelastic material, the reflected strain wave (reflected from the rear end of the input bar to the front end thereof and reflected from the rear end of the specimen to the front end of the input bar after the incident strain wave passes through the specimen) interferes with the second reflected strain wave (the incident strain wave reflected from the rear end of the input bar to the front end thereof from which it is reflected again). Thus, it is difficult to measure the reflected strain wave.

More specifically, in the case where the specimen is made of a soft material particularly, of the above-described reflected strain waves which are measured with the strain gauge installed on the input bar, before the damp of the reflected strain wave (hereinafter referred to as third reflected strain wave) which is reflected from the rear end of the specimen to the front end of the input bar after it passes through the specimen does not terminate, the strain gauge installed on the input bar measures the second reflected strain wave. That is, the second and third reflected strain waves interfere with each other. Thus it is difficult to measure the second and third reflected strain waves correctly.

In the case where the specimen is made of a very soft material particularly, the transmitted strain wave which has passed through the specimen has a longer period. In this case, before the damp of the transmitted strain wave which is measured with the output bar does not terminate, the transmitted strain wave is reflected from the rear end of the output bar and measured with the strain gauge. That is, both waves interfere with each other. Thus it is difficult to measure the transmitted reflected strain wave correctly.

SUMMARY OF THE INVENTION

The present invention has been made in view of the above-described situation. Thus, it is an object of the present invention to provide an apparatus and a method capable of correctly measuring a viscoelastic characteristic value of a specimen, even though the specimen is made of a particularly soft material.

To achieve the object, according to the present invention, there is provided A viscoelastic characteristic value-measuring apparatus having an input bar and an output bar arranged in a straight line to put a specimen therebetween; first and second strain gauges installed on said input bar; and third and fourth strain gauges installed on said output bar, wherein said first and second strain gauges measure an incident strain wave and a reflected strain wave generated on said input bar when a front end of said input bar is hit, and said third and fourth strain gauges measure a transmitted strain wave transmitted from said input bar to said output bar through said specimen; and a length of said input bar is set to not less than 1000 mm nor more than 2500 mm; a length of said output bar is set to not less than 700 mm nor more than 2200 mm; and a propagation speed of a strain in said input bar and said output bar is set to not less than 1200 m/s nor more than 1800 m/s.

In the viscoelastic characteristic value-measuring apparatus, the length of the input bar is set to not less than 1000 mm, and the propagation speed of a strain in the input bar and the output bar is set to not less than 1200 m/s nor more than 1800 m/s. Thus it takes much time for the second reflected strain wave (the incident strain wave reflected from the rear end of the input bar to the front end thereof from which it is reflected again) to reach the first and second strain gauges. Accordingly, before the second reflected strain wave reaches the first and second strain gauges, the first and second strain gauges are capable of measuring the third reflected strain wave (after passing through the specimen, reflected from the rear end of the specimen to the front end of the input bar). That is, it is possible to prevent the second and third reflected strain waves from interfering with each other. Thus it is possible to measure the third reflected strain wave correctly. From this point of view, it is most favorable that the length of the input bar is not less than 1500 mm.

The reason the propagation speed of the strain in the input bar and the output bar is set to not less than 1200 m/s nor more than 1800 m/s is because a material allowing the propagation speed of the strain to be less than 1200 m/s does not exist. If the propagation speed of the strain in the input bar and the output bar exceeds 1800 m/s, there is a big difference between the propagation speed of the strain in the input bar and the output bar and that of the strain in the specimen. That is, the propagation speed of the strain in the input bar and the output bar is higher than that of the strain in the specimen. Consequently the first and second strain gauges measure the third reflected strain wave passing through the input bar and the specimen and then reflected from the rear end of the specimen to the input bar. Further before the damp of the third reflected strain wave does not terminate, the first and second strain gauges measure the second reflected strain wave reflected at the rear end of the input bar and reflected again from the front end of the input bar. That is, the second and third reflected strain waves interfere with each other and hence an accurate analysis cannot be accomplished.

There is a case in which like the third reflected strain wave, the strain wave has a longer period after the strain wave passes through the specimen, depending on a material for the specimen. As the period of the third reflected strain wave becomes longer, it takes time increasingly to complete its damp. Thus the second and third reflected strain waves are liable to interfere with each other. Even in this case, because the propagation speed of the strain in the input bar and the output bar is set to the above-described range, the second reflected strain wave reaches the first and second strain gauges later than the third reflected strain wave. Therefore the second and third reflected strain waves do not interfere with each other.

The propagation speed of the strain in the input bar and the output bar is determined by the Young's modulus and the specific gravity (or density) of a material for the input bar and the output bar and does not depend on the configuration of the input bar and the output bar. As the Young's modulus becomes higher and as the specific gravity becomes smaller, the propagation speed becomes increasingly high. The propagation speed is computed based on the distance between the strain gauges installed on the input bar, the distance between the strain gauges installed on the output bar, and a passage period of time when a shock is applied to the input bar.

There is the following relationship among the propagation speed C0 (m/s) of the strain in the input bar and the output bar, the Young's modulus E (N/m$^2$) of the input bar and the output bar, and the density $\rho$ (kg/M$^3$) of the input bar and the output bar:

$$C0 = (E/\rho)^{1/2}.$$

Because in the viscoelastic characteristic value-measuring apparatus, the length of the output bar is set to not less than 700 mm, it takes much time for the transmitted strain wave which has been reflected from the rear end of the output bar to reach the strain gauges installed on the output bar. Accordingly, even though the period of the transmitted strain wave is long because the transmitted strain wave passes through the specimen, the strain gauges are capable of measuring the transmitted strain wave which has passed through the specimen (the damp of the transmitted strain wave terminates earlier), before the transmitted strain wave which has been reflected on the rear end of the output bar reaches the strain gauges. Thus it is possible to prevent the transmitted strain waves from interfering with each other. Thus it is possible to measure the transmitted strain wave correctly. From this point of view, it is most favorable that the length of the output bar is not less than 1500 mm.

In the viscoelastic characteristic value-measuring apparatus, the length of the input bar is set to less than 2500 mm and that of the output bar is set less than 2200 mm. This is because if the input bar and the output bar (stress bar) are too long, the stress bar is flexed by gravity. Consequently the surface of the stress bar is flexed. The flexure of the stress bar causes the strain wave to generate noise and makes it difficult for the input bar and the output bar to be coaxial with each other. Consequently the viscoelastic characteristic value is measured with low accuracy. From this point of view, it is more favorable that the length of the stress bar is set less than 2000 mm.

In the present invention, it is preferable that the input bar and the output bar (stress bar) are made of a polymer. It is possible to use polyacetal, polyethylene, and polypropylene as the material for the input bar and the output bar. Thereby there is a small difference between the propagation speed of the strain in the stress bar and that of the strain in the specimen also made of the polymer.

In the present invention, if the first and second strain gauges installed on the input bar are too close to the specimen, the first and second strain gauges measure the reflected strain wave reflected from the rear end of the input bar, before the damp of an incident strain wave terminates. That is, both the incident strain wave and the reflected strain wave interfere with each other. Thereby it is difficult to measure the incident strain wave correctly.

If the first and second strain gauges are too far from the specimen (i.e., if the first and second strain gauges are too close to the front end of the input bar), the second and first strain gauges measure the third reflected strain wave passing through the specimen and reflected from the rear end of the specimen to the front end of the input bar. The first and second strain gauges also measure the second reflected strain wave, before the damp of the third reflected strain wave does not terminate. That is, the second and third reflected strain waves interfere with each other. Hence it is difficult to measure the third reflected strain wave correctly.

From these points of view, it is preferable that the first strain gauge is installed on the input bar between a position spaced 500 mm from the rear end of the input bar and a position spaced 1100 mm from the rear end thereof and that the second strain gauge is installed on the input bar between a position spaced 250 mm from the rear end of the input bar and a position spaced 750 mm from the rear end thereof. If the interval between the first strain gauge and the second strain gauge is too close to each other, the degree of accuracy of the transmission function becomes low. Thus it is preferable that the first strain gauge and the second strain gauge are installed on the input bar at an interval not less than 200 mm.

To obtain viscoelastic characteristic values by using the viscoelastic characteristic value-measuring apparatus, the front end of the input bar is hit, with the specimen put between the rear end of the input bar and the front end of the output bar. As a result, the strain wave generated by the hitting propagates in the input bar, the specimen, and the output bar. The first and second strain gauges installed on the input bar measure the incident strain wave and the reflected strain wave (the reflected wave reflected from the rear end of the input bar to the front end of the input bar and the reflected wave reflected from the rear end of the specimen to the front end of the input bar after it passes through the specimen). The third and fourth strain gauges installed on the output bar measure the transmitted strain wave. Thereafter, the following histories are estimated by using a history of the each strain wave: a history of the incident strain wave at the rear end of the input bar, a history of the reflected strain wave at the rear end of the input bar, and a history of the transmitted strain wave at the front end of the output bar. Thereafter, a strain speed history of a specimen, a strain history thereof, and a stress history thereof are computed from the estimated history of the incident strain wave, the history of the reflected strain wave, and the history of the transmitted strain wave to determine a stress-strain curve of a specimen. Finally, viscoelastic characteristic values such as the Young's modulus, the loss factor, and the like are computed from the stress-strain curve.

In the measuring method of the present invention, in addition to the strain wave generated by hitting the input bar, a scattered wave generated by hitting the input bar is included as a component of a waveform to be measured by each gauge. The frequency of the strain wave is in the range of 1.5 kHz to 5.0 kHz, whereas the scattered wave is a high-frequency wave having a frequency higher than 10 kHz. The high-frequency wave is a noise. Thus, when a stress-strain curve of a specimen is drawn by using a synthesized wave including a noise, the degree of accuracy of an obtained viscoelastic characteristic value is low. Therefore, to improve the degree of accuracy of the viscoelastic characteristic value, it is preferable to make a correction for the synthesized wave. As means for making the correction, strain waves (synthesized wave) measured with the first, second, third, and fourth gauges are applied to a low-pass filter to remove the high-frequency wave having the frequency higher than 10 kHz.

In the case where the specimen is made of a soft material, the input bar and the output bar are liable to be uncoaxial with each other. To prevent this, it is preferable to set the length of the specimen to not less than 1 mm nor more than 5 mm. When the length of the specimen is shorter than the lower limit, a frictional force acting on the surface of the specimen and the stress bar in contact with the specimen and an inertial force acting radially in the specimen cannot be ignored. In this case, the magnitude of a measurement error may be large. On the other hand, when the length of the specimen is longer than the upper limit, there is a possibility that the curve of obtained strain history and stress history are irregular.

DETAILED DESCRIPTION OF THE PREFERRED EMBODIMENTS

The embodiment of the present invention will be described below with reference to the drawings.

Figure 1:
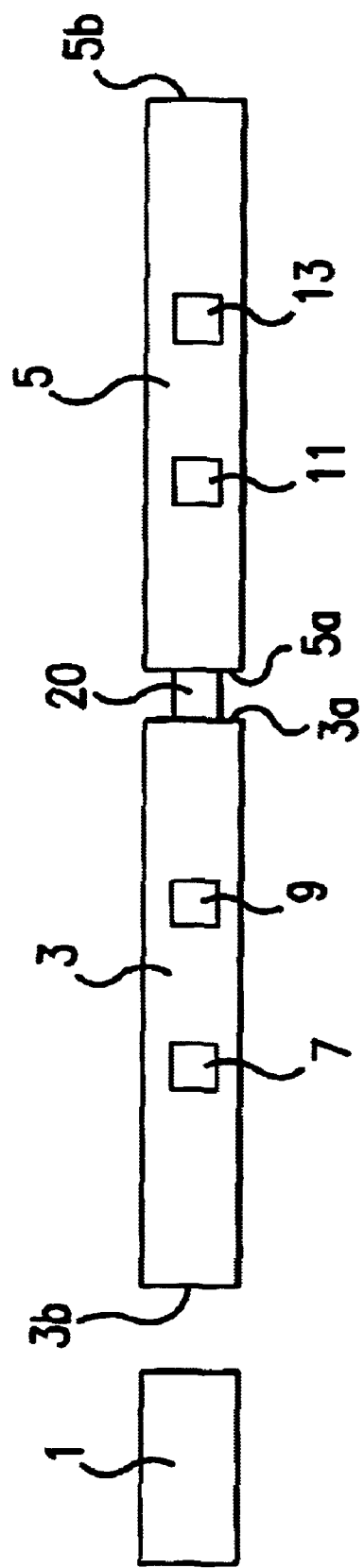
FIG. 1 is an illustrative front view showing a viscoelastic characteristic value-measuring apparatus according to an embodiment of the present invention.

FIG. 1 is an illustrative front view showing a viscoelastic characteristic value-measuring apparatus according to an embodiment of the present invention. The viscoelastic characteristic value-measuring apparatus has a impact bar 1, an input bar 3, and an output bar 5. A first strain gauge 7 and a second strain gauge 9 are installed on the input bar 3. A third strain gauge 11 and a fourth strain gauge 13 are installed on the output bar 5. A disk-shaped specimen 20 made of a viscoelastic material is put between a rear end 3a of the input bar 3 and a front end 5a of the output bar 5.

The impact bar 1, the input bar 3, and the output bar 5 are cylindrical and made of polyacetal. The propagation speed of a strain in the input bar 3 and the output bar 5 is set to 1450 m/s. The sectional diameter of each of the first bar 3 and the output bar 5 is set to 20 mm. The length of the impact bar 1 is set to 100 mm. The length of each of the input bar 3 and the output bar 5 is set to 2000 mm. The first strain gauge 7 is installed on the input bar 3 at a position spaced 900 mm from the rear end 3a thereof. The second strain gauge 9 is installed on the input bar 3 at a position spaced 600 mm from the rear end 3a thereof. The third strain gauge 11 is installed on the output bar 5 at a position spaced 300 mm from the front end 5a thereof. The fourth strain gauge 13 is installed on the output bar 5 at a position spaced 600 mm from the front end 5a thereof. The length of the specimen 20, namely, the distance between the rear end 3a of the input bar 3 and the front end 5a of the output bar 5 is set to 4 mm. The sectional diameter of the specimen 20 is set to 18 mm.

In measuring the viscoelastic characteristic value of the specimen with the viscoelastic characteristic value-measuring apparatus, initially, the specimen 20 is put between the input bar 3 and the output bar 5, with the front end surface of the specimen 20 in close contact with the rear end 3a of the input bar 3 and with the rear end surface of the specimen 20 in close contact with the front end 5a of the output bar 5. In this state, the impact bar 1 is brought into collision with the front end 3b of the input bar 3. Thereby, an incident strain wave is generated in the input bar 3. The incident strain wave advances to the rear end 3a of the input bar 3. A part of the incident strain wave is reflected from the rear end 3a of the input bar 3 to generate a reflected strain wave. A part of the incident strain wave passes through the specimen 20 and is reflected from the rear end of the specimen 20 to generate a reflected strain wave. Both reflected strain waves advance to the front end 3b of the input bar 3. A part of the incident strain wave advances to the specimen 20 from the rear end 3a of the input bar 3 and propagates to the output bar 5 to generate a transmitted strain wave. The transmitted strain wave advances to the rear end 5b of the output bar 5.

The incident strain wave is measured with the first strain gauge 7 and the second strain gauge 9. The incident strain wave is passed through a low-pass filter to remove a high-frequency wave having a frequency more than 10 KHz from the incident strain wave. Zero compensation is performed to make the base line value of the history of the incident strain wave zero. Fourier transformation of an obtained time base strain at each of the first strain gauge 7 and the second strain gauge 9 is performed to determine a frequency axis strain. A transmission function is derived from the frequency axis strain at the first strain gauge 7 and the second strain gauge 9. The frequency axis strain at the rear end 3a of the input bar 3 is estimated in consideration of the ratio of the distance X1 between the first strain gauge 7 and the rear end 3a of the input bar 3 to the distance X2 between the second strain gauge 9 and the rear end 3a of the input bar 3 and based on the transmission function. Fourier inverse transformation of the frequency axis strain is performed to obtain a time base strain (history of strain) $\epsilon i$ of the incident strain wave at the rear end 3a of the input bar 3.

Similarly, the second strain gauge 9 and the first strain gauge 7 measure the reflected strain wave reflected from the rear end 3a of the input bar 3 to the front end 3b of the input bar 3 and also the reflected strain wave reflected from the rear end of the specimen 20 to the front end 3b of the input bar 3 after it passes through the specimen 20. A time base strain (history of strain) $\epsilon r$ of the reflected strain wave at the rear end 3a of the input bar 3 is obtained from the measured reflected strain wave.

The transmitted strain wave which propagates to the output bar 5 through the specimen 20 is measured with the third strain gauge 11 and the fourth strain gauge 13 installed on the output bar 5. A time base strain (history of strain) $\epsilon t$ of the transmitted strain wave at the front end 5a of the output bar 5 is obtained from the measured transmitted strain wave.

From the obtained time base strains $\epsilon i$, $\epsilon r$, and $\epsilon t$, a strain speed $\epsilon'$ of the specimen 20 is computed by using an equation (1) shown below.

$$\epsilon' = (C0/L) \cdot (\epsilon i - \epsilon r - \epsilon t) \tag{1}$$

where C0 indicates the propagation speed (m/s) of the strain in the stress bar; and L indicates the length (m) of the specimen.

From the time base strains $\epsilon i$, $\epsilon r$, and $\epsilon t$, the strain $\epsilon$ of the specimen 20 is computed by using an equation (2) shown below.

$$\varepsilon = (C0/L) \cdot \int_0^t (\varepsilon_1 - \varepsilon_r - \varepsilon_t) dt \tag{2}$$

where C0 indicates the propagation speed (m/s) of the strain in the stress bar; and L indicates the length (m) of the specimen.

From the time base strains $\epsilon i$, $\epsilon r$, and $\epsilon t$, a stress $\sigma$ of the specimen 20 is computed by using an equation (3) shown below.

$$\begin{aligned}\sigma &= (E \cdot A / (2As)) \cdot (\varepsilon i + \varepsilon r + \varepsilon t) \\ &= (E \cdot D^2 / (2(Ds)^2)) \cdot (\varepsilon i + \varepsilon r + \varepsilon t)\end{aligned} \tag{3}$$

where E indicates the Young's modulus (N/m$^2$) of the stress bar; A indicates the sectional area (m$^2$) of the stress bar; As indicates the sectional area (m$^2$) of the specimen; D indicates the diameter (m) of the stress bar; and Ds indicates the diameter (m) of the specimen.

Figure 2:
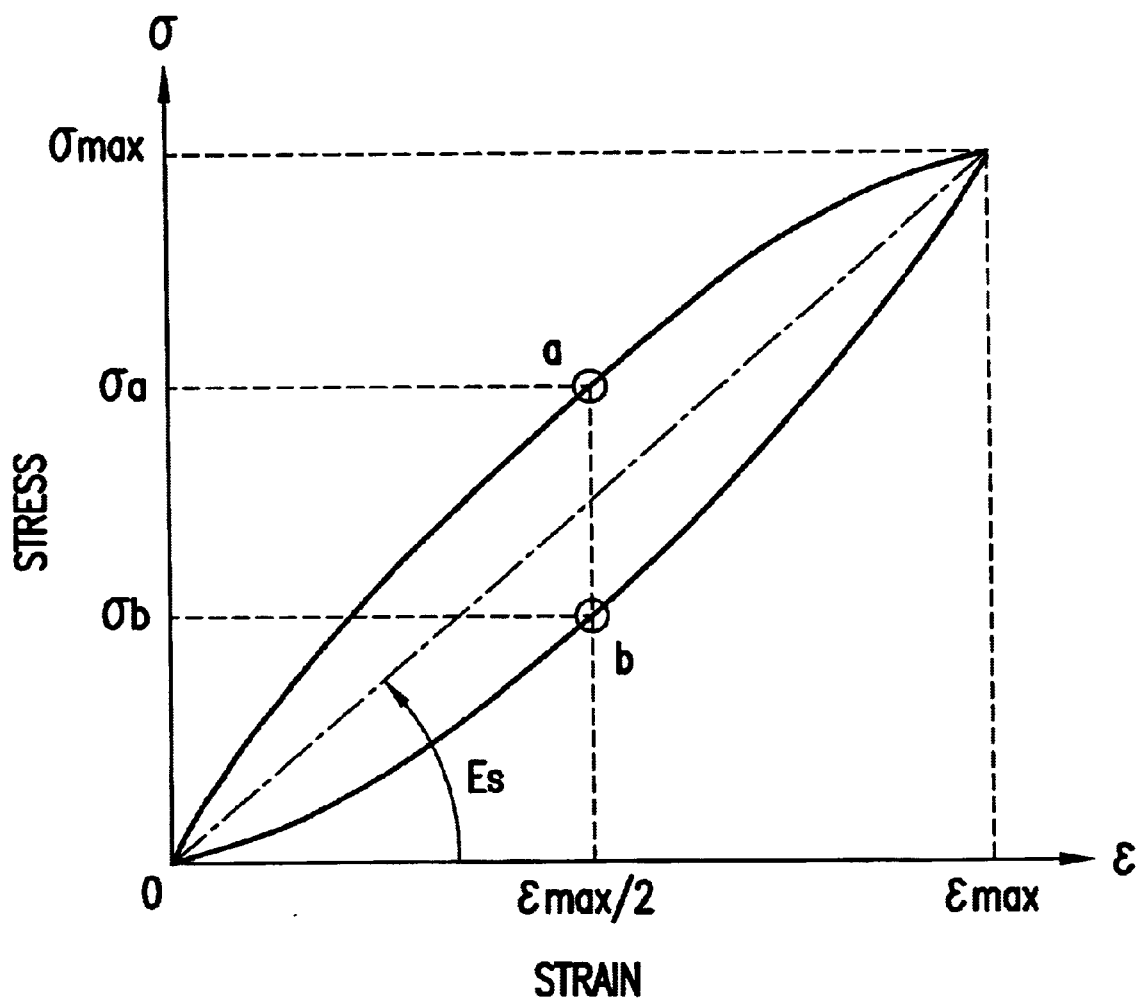
FIG. 2 is a graph showing a typical stress-strain curve.

FIG. 2 is a graph showing a typical stress-strain curve. From the stress-strain curve, the Young's modulus Es of the specimen 20 is computed by using an equation (4) shown below.

$$Es = \sigma \max / \epsilon \max \tag{4}$$

From the stress-strain curve of FIG. 2, a phase angle $\delta$ is computed by using an equation (5) shown below:

$$\delta = \sin^{-1}((\sigma a - \sigma b)/\sigma \max) \tag{5}$$

A loss factor (tan $\delta$) is computed from the phase angle $\delta$.

EXAMPLE

Figure 3:
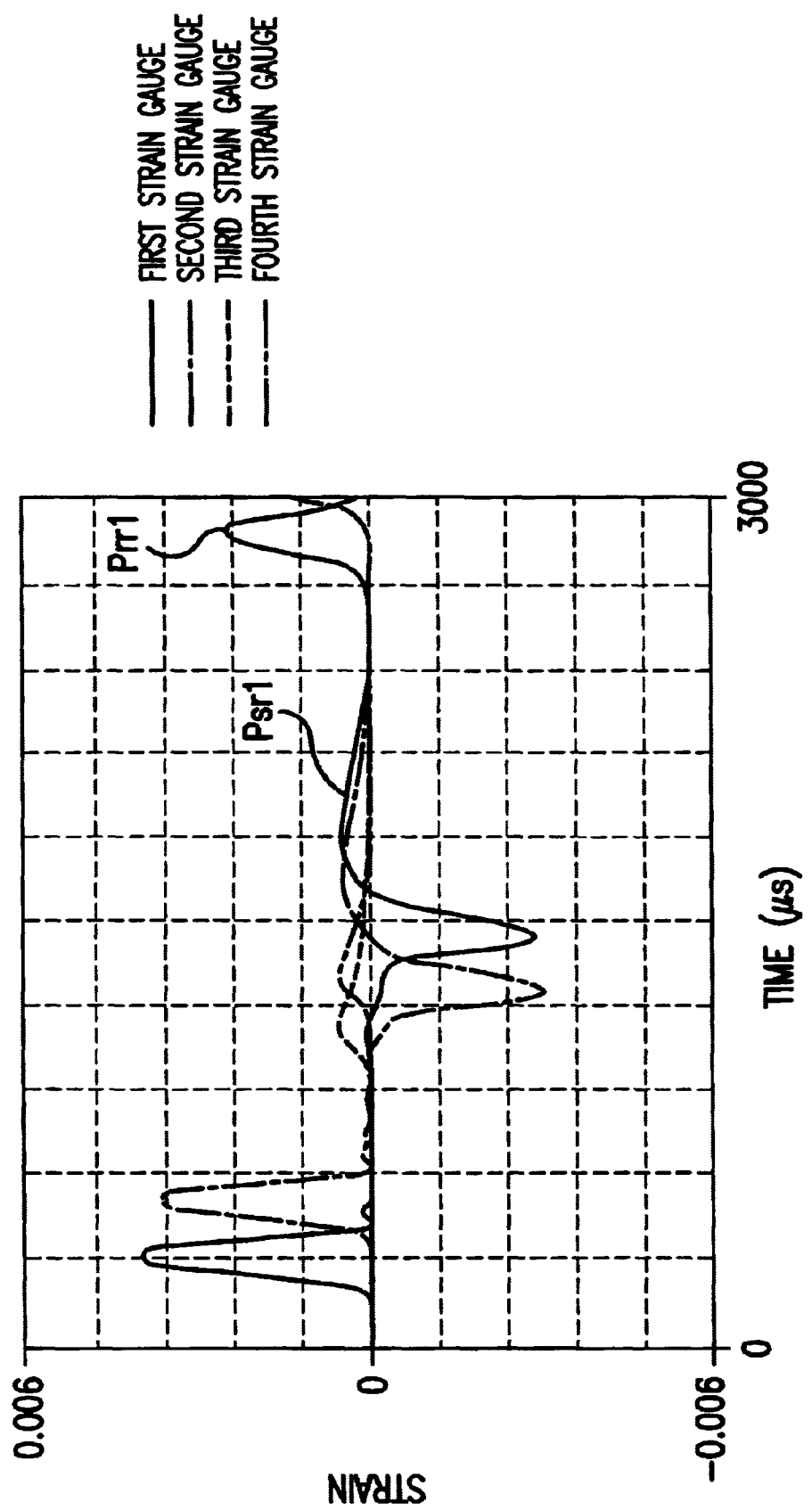
FIG. 3 is a graph showing a strain wave measured by a viscoelastic characteristic value-measuring apparatus of an embodiment of the present invention.

A viscoelastic characteristic values of a specimen was measured by using the viscoelastic characteristic value-measuring apparatus (length of each of input bar and output bar was 2000 mm) shown in FIG. 1. The specimen was made of synthetic resin having a JA hardness of 70. The collision speed of the impact bar was 14 m/s. As the measuring condition, the room temperature was set to 23° C., and the relative humidity was set to 50%. FIG. 3 shows an incident strain wave and a reflected strain wave measured with the first strain gauge and the second strain gauge, and transmitted strain waves measured with the third strain gauge and the fourth strain gauge. Each of the input bar and the output bar was made of polyacetal (propagation speed of strain: 1450 m/s).

Comparison Example

Figure 4:
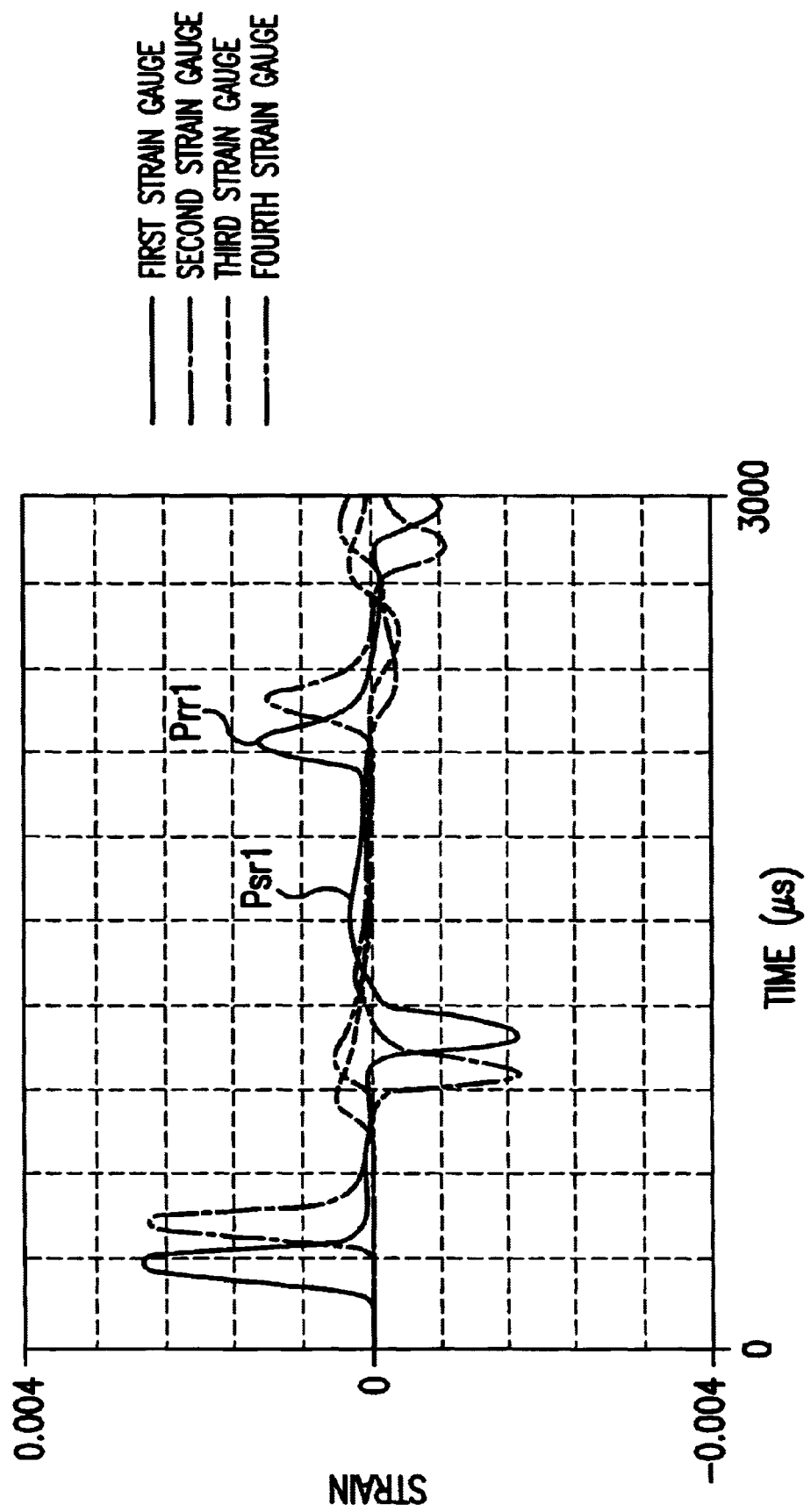
FIG. 4 is a graph showing a strain wave measured by a viscoelastic characteristic value-measuring apparatus of a comparison example.

A viscoelastic characteristic values of a specimen was measured by a method similar to the above-described method except that the input bar and the output bar were made of polymethyl methacrylate (propagation speed: 2200 m/s). FIG. 4 shows strain waves measured with the first strain gauge, the second strain gauge, the third strain gauge, and the fourth strain gauge.

As shown in FIG. 4 showing measured results of the comparison example, the first strain gauge measured a peak Psr1 of a third reflected strain wave which passed through the input bar and the specimen and was reflected from the rear end of the specimen to the input bar and a peak Prr1 of a second reflected strain wave reflected from the rear end of the input bar and then reflected again from the front end of the input bar. From the result shown in FIG. 4, before the damp of the third reflected strain wave did not terminate, the first strain gauge measured the second reflected strain wave. This indicates that there was a possibility that the second and third reflected strain waves interfered with each other.

On the other hand, the measured results of the example of the present invention are as shown in FIG. 3. The propagation speed of the strain in the stress bar is set to 1450 m/s. After the damp of the peak Psr1 of the third reflected strain wave which passed through the input bar and the specimen and was reflected from the rear end of the specimen to the input bar completely terminates (value of strain becomes zero), the first strain gauge measured the peak Prr1 of the second reflected strain wave reflected from the rear end of the input bar and reflected again from the front end of the input bar. It was confirmed that the second and third reflected strain waves did not interfere with each other. Further, it was also confirmed that because the length of the input bar and that of the output bar were within the specified range, other interferences of the strain waves did not occur and that each strain wave could be measured with high accuracy.

As described above, the conventional viscoelastic characteristic value-measuring apparatus using the split Hopkinson's bar is capable of correctly measuring viscoelastic characteristic values of a comparatively hard polymer when a maximum strain speed is as high as 100–8000 per second and when a maximum deformation amount is as large as 0.1%–30%. However the conventional viscoelastic characteristic value-measuring apparatus is incapable of correctly measuring viscoelastic characteristic values of a soft polymer made of rubber or resin, because strain waves detected by the strain gauges interfere each other. On the other hand, in the viscoelastic characteristic value-measuring apparatus of the present invention using the split Hopkinson's bar, the length of the input bar and that of the output bar and the propagation speed of the strain in the input bar and the output bar are specified to a predetermined value respectively to prevent interference of strain waves which are detected with the strain gauges installed on the input bar and that of the output bar. Therefore, the viscoelastic characteristic value-measuring apparatus of the present invention can measure the viscoelastic characteristic values of the soft polymer correctly.

What is claimed is:

1. A viscoelastic characteristic value-measuring apparatus having an input bar and an output bar arranged in a straight line to put a specimen therebetween; first and second strain gauges installed on said input bar: and third and fourth strain gauges installed on said output bar, wherein said first and second strain gauges measure an incident strain wave and a reflected strain wave generated on said input bar when a front end of said input bar is hit, and said third and fourth strain gauges measure a transmitted strain wave transmitted from said input bar to said output bar through said specimen; and a length of said input bar is set to not less than 1000 mm nor more than 2500 mm; a length of said output bar is set to not less than 700 mm nor more than 2200 mm; and a propagation speed of a strain in said input bar and said output bar is set to not less than 1200 m/s nor more than 1800 m/s, and is set to be a small difference between the propagation speed of the strain in the input bar and the output bar and that of the strain in the specimen, in order to measure correctly a third reflected strain wave which is reflected from the rear end of the specimen to the front end of the input bar, preventing the third reflected strain waves and a second reflected strain wave which is reflected again from the front end of the input bar to the rear end of the input bar from interfering with each other.

2. The measuring apparatus according to claim 1, wherein said input bar and said output bar are made of a polymer respectively.

3. The measuring apparatus according to claim 1, wherein said first strain gauge is installed on said input bar between a position spaced 500 mm from a rear end of said input bar and a position spaced 1100 mm from said rear end of said input bar; and said second strain gauge is installed on said input bar between a position spaced 250 mm from said rear end of said input bar and a position spaced 750 mm from said rear end of said input bar.

4. The measuring apparatus according to claim 3, wherein said first strain gauge and said second strain gauge are installed on said input bar by spacing said first strain gauge and said second strain gauge at an interval not less than 200 mm.

5. A method of measuring a viscoelastic characteristic value by using the viscoelastic characteristic value-measuring apparatus according to claim 1, comprising the steps of:

hitting a front end of an input bar, with a specimen put between a rear end of said input bar and a front end of an output bar;

measuring an incident strain wave propagating in said input bar and a reflected strain wave propagating in said input bar with first and second strain gauges installed on said input bar, and measuring a transmitted strain wave propagating, and said output bar with third and fourth strain gauges installed on said output bar;

estimating a history of said incident strain wave at said rear end of said input bar, a history of said reflected strain wave at said rear end of said input bar, and a history of said transmitted strain wave at said front end of said output bar by using a history of said each strain wave;

computing a strain speed history of a specimen, a strain history thereof, and a stress history thereof from said estimated history of said incident strain wave, said history of said reflected strain wave, and said history of said transmitted strain wave and determining a stress-strain curve of a specimen; and computing a viscoelastic characteristic value from said stress-strain curve.

6. The method according to claim 5, wherein a correction is performed which removes a high-frequency wave having a frequency more than 10 KHz from said incident strain wave, said reflected strain wave, and said transmitted strain wave measured with said first, second, third, and fourth strain gauges.

7. The method according to claim 5, wherein a length of said specimen is set to not less than 1 mm nor more than 5 mm.

8. The method according to claim 5, wherein the viscoelastic characteristic value is computed as a Young's modulus.

9. The method according to claim 5, wherein the viscoelastic characteristic value is computed as a loss factor.

* * * * *

UNITED STATES PATENT AND TRADEMARK OFFICE
CERTIFICATE OF CORRECTION

PATENT NO. : 6,672,141 B2  
APPLICATION NO. : 09/951215  
DATED : January 6, 2004  
INVENTOR(S) : Kiyoto Maruoka et al.

It is certified that error appears in the above-identified patent and that said Letters Patent is hereby corrected as shown below:

<u>Title page,</u>
Item [75], add -- and Noritoshi Nakagawa, Higashihiroshima-shi (JP) --.

Signed and Sealed this

Thirteenth Day of February, 2007

JON W. DUDAS
*Director of the United States Patent and Trademark Office*